United States Patent
Holder et al.

(10) Patent No.: US 9,689,247 B2
(45) Date of Patent: Jun. 27, 2017

(54) LOCATION AND STIMULATION METHODS AND APPARATUSES UTILIZING DOWNHOLE TOOLS

(71) Applicants: Superior Energy Services, LLC, Harvey, LA (US); A O International II, Inc., Stafford, TX (US)

(72) Inventors: Barry Kent Holder, Montgomery, TX (US); Andre Orban, Sugarland, TX (US); Daniel Maurice Lerner, Missouri City, TX (US)

(73) Assignees: Superior Energy Services, LLC, Harvey, LA (US); A O International, II LLC, Stafford, TX (US)

( * ) Notice: Subject to any disclaimer, the term of this patent is extended or adjusted under 35 U.S.C. 154(b) by 216 days.

(21) Appl. No.: 14/668,598

(22) Filed: Mar. 25, 2015

(65) Prior Publication Data
US 2015/0275643 A1 Oct. 1, 2015

Related U.S. Application Data

(60) Provisional application No. 61/970,563, filed on Mar. 26, 2014, provisional application No. 61/970,775, filed on Mar. 26, 2014.

(51) Int. Cl.
| | |
|---|---|
| *E21B 33/12* | (2006.01) |
| *E21B 43/263* | (2006.01) |
| *E21B 47/00* | (2012.01) |
| *G01B 21/08* | (2006.01) |
| *G01N 21/00* | (2006.01) |

(Continued)

(52) U.S. Cl.
CPC ............ *E21B 43/263* (2013.01); *E21B 47/00* (2013.01); *G01B 21/08* (2013.01); *G01N 21/00* (2013.01); *G01N 23/00* (2013.01); *G01N 27/02* (2013.01); *G01N 27/26* (2013.01); *G01N 27/72* (2013.01); *G01N 29/04* (2013.01)

(58) Field of Classification Search
CPC ............ E21B 43/11852; E21B 43/263; E21B 34/063; E21B 43/116; E21B 43/1185; E21B 43/119; E21B 43/14
See application file for complete search history.

(56) References Cited

U.S. PATENT DOCUMENTS

| | | | |
|---|---|---|---|
| 2,201,290 A | 5/1940 | Greene | |
| 2,621,895 A | 12/1952 | Toelke | |

(Continued)

FOREIGN PATENT DOCUMENTS

| | | |
|---|---|---|
| WO | 99/14524 A2 | 3/1999 |
| WO | 2012/161854 A2 | 11/2012 |

OTHER PUBLICATIONS

PCT Application No. US2015/022479; International Search Report for Applicant Superior Energy Services, LLC, et al dated Aug. 10, 2015.

*Primary Examiner* — Daniel P Stephenson
(74) *Attorney, Agent, or Firm* — Jones Walker LLP

(57) ABSTRACT

A propellant tool for use in a hydrocarbon bearing formation. The tool includes a tubular body having a connector on each end for connection with other tubular members within a tubular string. A coded marker is positioned on the tubular body and a propellant chamber is positioned on an outside surface of the tubular body. A propellant ignition mechanism positioned on the tubular body for igniting the propellant in the propellant chamber.

35 Claims, 12 Drawing Sheets

(51) Int. Cl.
*G01N 23/00* (2006.01)
*G01N 27/02* (2006.01)
*G01N 27/26* (2006.01)
*G01N 27/72* (2006.01)
*G01N 29/04* (2006.01)

(56) References Cited

U.S. PATENT DOCUMENTS

| | | |
|---|---|---|
| 2,667,836 A | 2/1954 | Church et al. |
| 3,106,960 A | 10/1963 | Doak |
| 3,198,255 A | 8/1965 | Ownby |
| 3,468,386 A | 9/1969 | Johnson |
| 3,513,912 A | 5/1970 | Boop |
| 4,244,424 A | 1/1981 | Talbot |
| 4,572,293 A | 2/1986 | Wilson et al. |
| 4,578,991 A | 4/1986 | Nowlin |
| 4,722,392 A | 2/1988 | Proctor et al. |
| 4,798,244 A | 1/1989 | Trost |
| 5,224,556 A | 7/1993 | Wilson et al. |
| 5,355,957 A * | 10/1994 | Burleson ............ E21B 43/11852 166/297 |
| 5,505,260 A | 4/1996 | Andersen et al. |
| 5,513,703 A | 5/1996 | Mills et al. |
| 5,691,502 A * | 11/1997 | Craddock ................ F42B 12/32 102/389 |
| 5,775,426 A | 7/1998 | Snider et al. |
| 5,823,266 A * | 10/1998 | Burleson ................ E21B 17/06 166/242.6 |
| 5,996,711 A | 12/1999 | Ohmer |
| 6,009,947 A | 1/2000 | Wilson et al. |
| 6,012,527 A | 1/2000 | Nitis et al. |
| 6,220,355 B1 | 4/2001 | French |
| 6,536,524 B1 | 3/2003 | Snider |
| 6,557,636 B2 | 5/2003 | Cernocky et al. |
| 6,568,480 B2 | 5/2003 | Dewey |
| 6,817,298 B1 | 11/2004 | Zharkov et al. |
| 6,886,466 B2 | 5/2005 | Senules |
| 7,073,582 B2 | 7/2006 | Connell et al. |
| 7,073,589 B2 | 7/2006 | Tiernan et al. |
| 7,096,954 B2 | 8/2006 | Weng et al. |
| 7,152,676 B2 | 12/2006 | Vella et al. |
| 7,165,614 B1 | 1/2007 | Bond |
| 7,240,738 B2 | 7/2007 | Pendleton |
| 7,267,172 B2 | 9/2007 | Hofman |
| 7,273,102 B2 | 9/2007 | Sheffield |
| 7,278,484 B2 | 10/2007 | Vella et al. |
| 7,353,866 B2 * | 4/2008 | Snider ................... E21B 43/263 166/297 |
| 7,493,958 B2 | 2/2009 | Hromas et al. |
| 7,503,398 B2 | 3/2009 | LoGiudice et al. |
| 7,546,875 B2 | 6/2009 | Whitsitt et al. |
| 7,656,161 B2 | 2/2010 | McElhinney |
| 7,681,645 B2 | 3/2010 | McMillin et al. |
| 7,753,121 B2 * | 7/2010 | Whitsitt ................ E21B 43/045 166/233 |
| 7,802,627 B2 | 9/2010 | Hofman et al. |
| 7,926,571 B2 | 4/2011 | Hofman |
| 8,044,820 B2 | 10/2011 | Snider et al. |
| 8,127,832 B1 | 3/2012 | Bond |
| 8,381,807 B2 * | 2/2013 | Jackson ................ E21B 43/263 166/317 |
| 8,393,392 B2 * | 3/2013 | Mytopher ............. E21B 34/063 166/297 |
| 8,479,823 B2 | 7/2013 | Mireles |
| 8,505,632 B2 | 8/2013 | Guerrero et al. |
| 8,517,113 B2 | 8/2013 | Sheffield |
| 9,416,598 B2 * | 8/2016 | Birch ................... E21B 17/1035 |
| 9,453,402 B1 * | 9/2016 | Barton ................... E21B 43/26 |
| 2003/0000703 A1 * | 1/2003 | Cernocky ............... E21B 47/12 166/297 |
| 2003/0090390 A1 | 5/2003 | Snider et al. |
| 2003/0173089 A1 | 9/2003 | Westgard et al. |
| 2004/0206503 A1 | 10/2004 | Bell et al. |
| 2006/0048664 A1 * | 3/2006 | Tiernan ................. E21B 43/263 102/332 |
| 2007/0285275 A1 | 12/2007 | Purkis et al. |
| 2009/0071651 A1 | 3/2009 | Patel |
| 2009/0223663 A1 | 9/2009 | Snider et al. |
| 2009/0223670 A1 | 9/2009 | Snider |
| 2010/0230104 A1 * | 9/2010 | Nolke ..................... E21B 33/14 166/297 |
| 2011/0103173 A1 | 5/2011 | May |
| 2011/0139433 A1 | 6/2011 | Jackson et al. |
| 2011/0185806 A1 | 8/2011 | Pfutzner |
| 2013/0002255 A1 | 1/2013 | Shampine |
| 2013/0025883 A1 | 1/2013 | Robertson et al. |
| 2013/0255939 A1 | 10/2013 | Kumaran et al. |
| 2014/0060803 A1 * | 3/2014 | Gano ...................... E21B 23/01 166/66.5 |
| 2015/0007994 A1 * | 1/2015 | Lancaster ............. E21B 43/263 166/297 |
| 2015/0275643 A1 * | 10/2015 | Holder ................... E21B 43/263 166/63 |

* cited by examiner

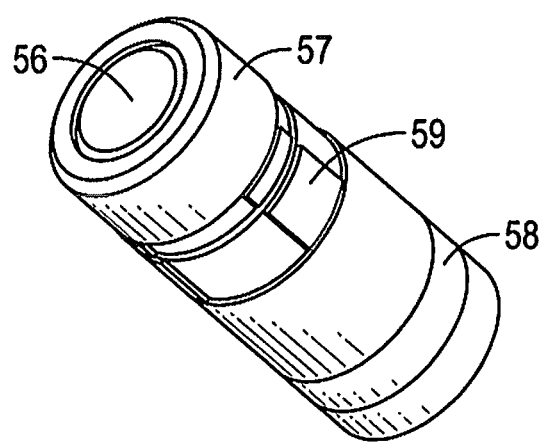
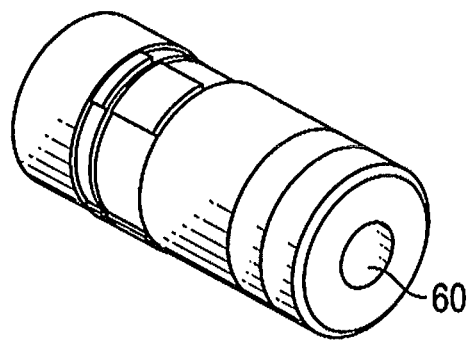
FIG. 4A                FIG. 4B
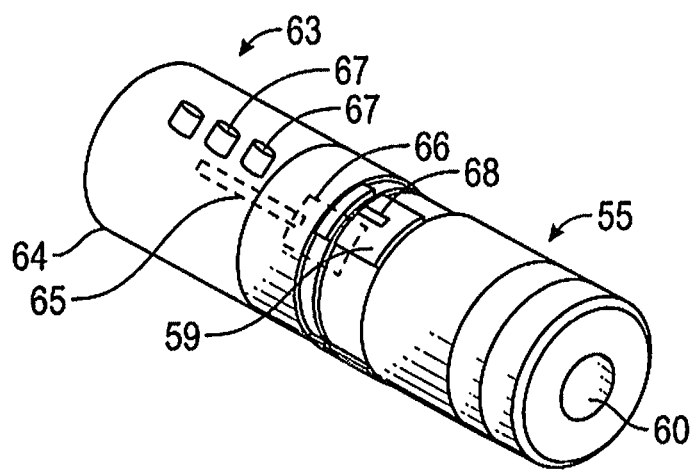
FIG. 4C

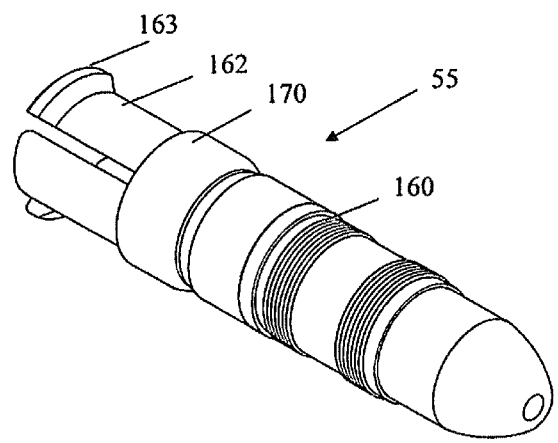
FIG. 10
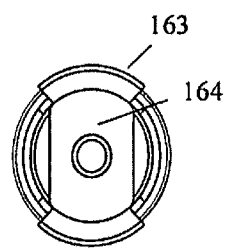
FIG. 11A
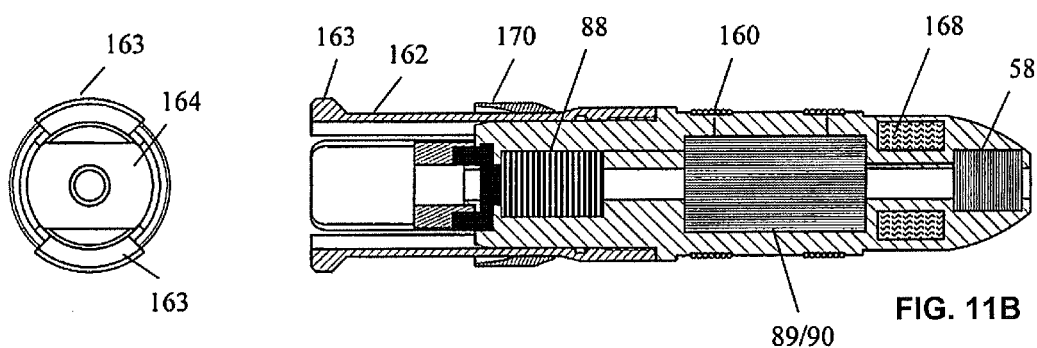
FIG. 11B
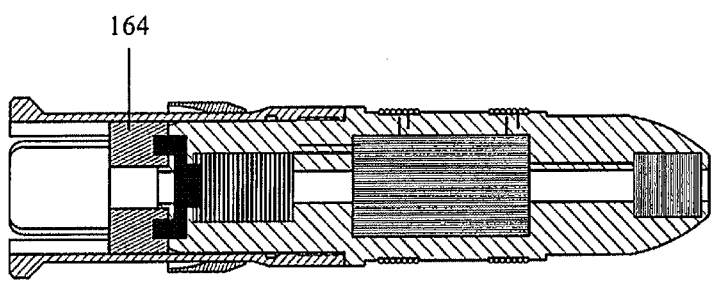
FIG. 12A
FIG. 12B

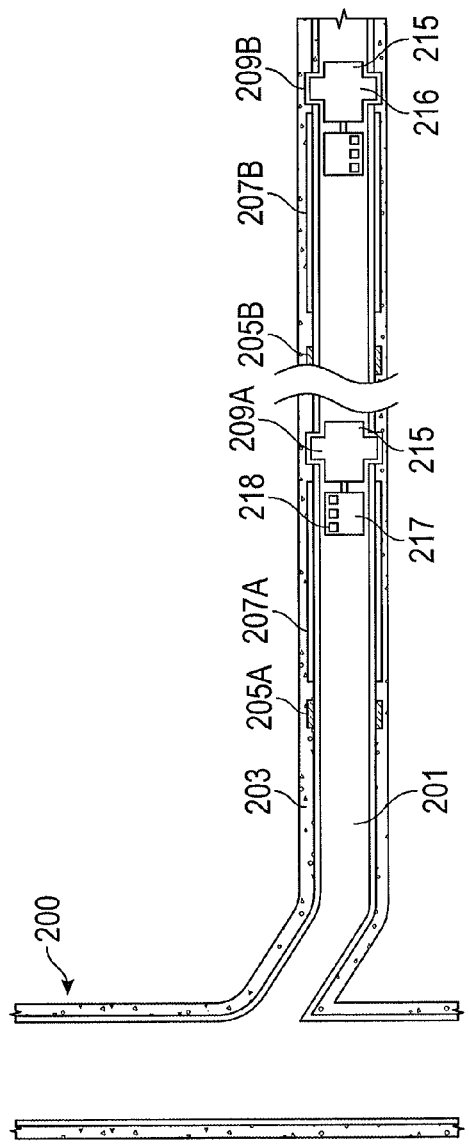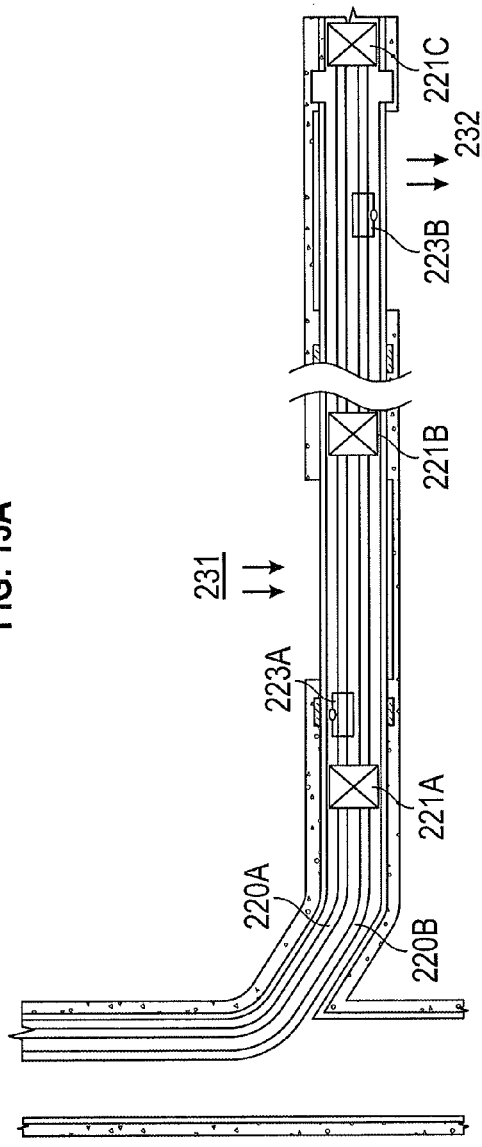

LOCATION AND STIMULATION METHODS AND APPARATUSES UTILIZING DOWNHOLE TOOLS

CROSS-REFERENCE TO RELATED APPLICATION

This application claims the benefit under 35 USC 119(e) of U.S. provisional application No. 61/970,563 filed Mar. 26, 2014 and 61/970,775 filed Mar. 26, 2014, both of which are incorporated by reference herein in their entirety.

BACKGROUND OF INVENTION

The present application concerns apparatuses and methods related to recovering hydrocarbons from underground formations. After a wellbore has been drilled through the hydrocarbon containing formation, a series of steps are generally taken to prepare the wellbore and the surrounding formation for the actual removal of hydrocarbons from the well. This is generally known as the "completion" stage of the hydrocarbon production process. Hydraulic fracturing and other formation stimulation procedures are often performed in the completion stage. However, hydraulic fracturing is a water intensive operation and has raised environmental concerns. It would be an improvement in the completion industry if techniques may be developed which enhance hydraulic fracturing or in some cases, substitute for hydraulic fracturing. The use of propellants to stimulate and/or fracture formations, either alone or in combination with hydraulic fracturing, is a promising area for such improvements.

SUMMARY OF SELECTED EMBODIMENTS OF INVENTION

One embodiment described herein is a tubular string for positioning in a wellbore. The tubular string includes a plurality of markers positioned along the tubular string; a plurality of propellant chambers positioned on an outside surface of the tubular string, each propellant chamber being in the vicinity of a marker; and a propellant ignition circuit associated with each propellant chamber.

Another embodiment is stimulation tool. The stimulation tool includes at least one tubular segment having end connectors for assembly into a larger tubular string; a propellant containment structure positioned on an outer surface of the tubular segment in a generally concentric orientation; a propellant positioned within the containment structure; and at least one burst disc positioned on the tubular segment, the burst disc configured to rupture at or below a peak pressure produced igniting the propellant.

A still further embodiment is a method of stimulating a subterranean formation. The method includes the steps of running a casing conveyed stimulation tool into a wellbore formed through the formation, where the stimulation tool includes at least one casing segment; a concentrically formed sleeve positioned on the casing segment; and a nondirected propellant positioned within the sleeve with substantially no directed force charges within the sleeve. The stimulation tool is cemented within the wellbore and then the propellant is ignited to induce a stimulation force in the formation which is substantially uniform along the length of the sleeve.

The foregoing are merely a few examples of the many embodiments described in the following Detailed Description and should not be considered as a limitation on the other embodiments described explicitly or implicitly herein.

BRIEF DESCRIPTION OF DRAWINGS

FIGS. 4A to 4C are views of an intelligent plug utilized with certain embodiments of the invention.

FIG. 10 is a perspective view of the intelligent plug seen in FIG. 9.

FIGS. 11B and 12B are cross-sectional views of the plug seen in FIG. 9.

FIGS. 11A and 12A are end views of a locking mechanism for the plug seen in FIGS. 11B and 12B.

FIGS. 13A and 13B illustrate different steps in one method embodiment of the present invention.

DETAILED DESCRIPTION OF SELECTED EMBODIMENTS

Figure 1:
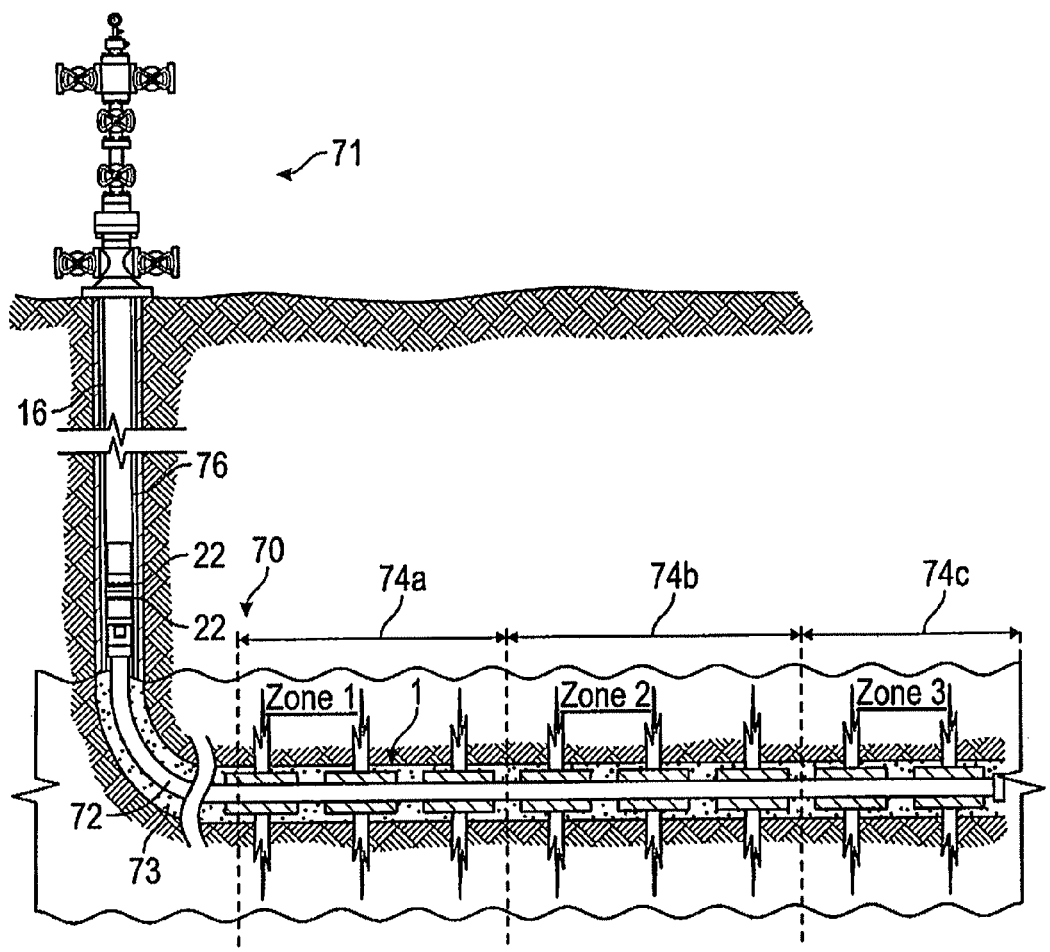
FIG. 1 illustrates one embodiment of the invention positioned in a well bore.

FIG. 1 illustrates one environment in which many embodiments of the present invention could be utilized. A production well 70 is drilled into a subterranean formation to access a hydrocarbon production formation 74. A well casing 76 is held in place in the production well 70 by cement 73 and a wellhead 71 is connected to the casing 76 at the surface. Connected to the lower end of the production well casing 16 is a liner hanger 22 connecting to production tubing 72, which is also shown cemented into the wellbore. In FIG. 1, the production formation 74 is segregated into multiple zones 74a, 74b, 74c, etc. As is known in the art, it is often advantageous to isolate, stimulate, and produce the zones separately. This requires selectively positioning tools downhole to open specific valves and to carry out stimulation activities in specific zones. As used in this disclosure, "up" means the direction along the wellbore toward the surface and "down" means in the direction toward the toe of the wellbore. Because the wellbore may often be deviated or horizontal, "up" or "down" should not be assumed to be in the vertical direction or to even have a vertical component. Likewise, describing a first tool component as "above" or "below" a second tool component means the first tool component is closer to or further from the surface, respectively, along the wellbore path (when the tool assembly is positioned in the wellbore) than the second tool component.

One embodiment of the present invention is a method of treating a hydrocarbon producing zone in a subterranean formation. Generally this method comprises the steps of running a stimulation tool 1 into the wellbore at the desired location or production zone, and igniting a propellant within the stimulation tool in order to induce a simulating force in the formation. In some embodiments, the stimulation tool will be employed in open hole wellbores, in other embodiments, the stimulation tool is cemented into the wellbore prior to ignition of the propellant.

Figure 2:
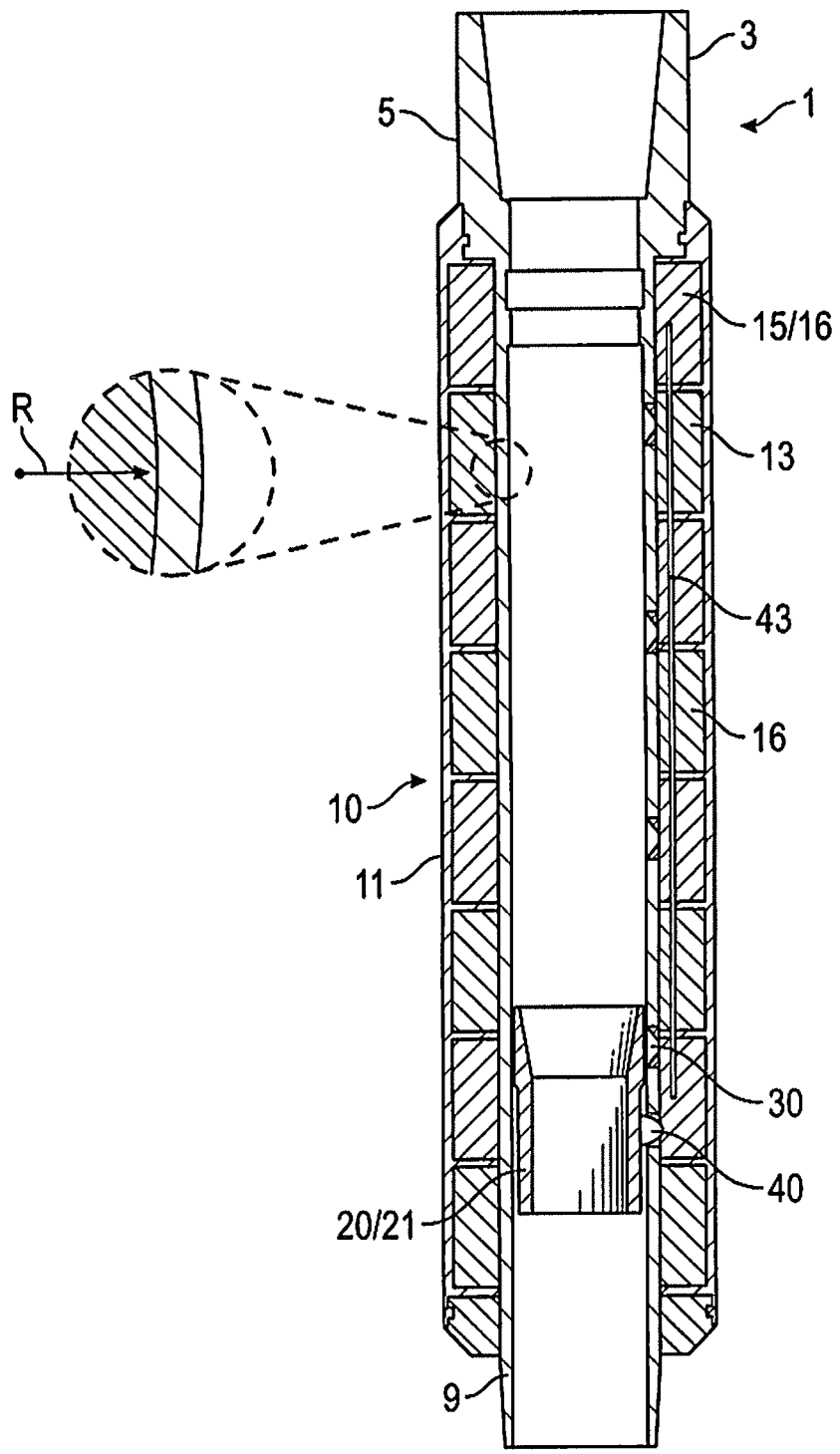
FIG. 2 is a cross-sectional view of one stimulation tool embodiment of the present invention.

The structure of one embodiment of the stimulation tool is seen in FIG. 2. This stimulation tool 1 will generally comprise at least one tubular segment 3 having end connectors for assembly into a larger tubular string (such as seen in FIG. 1). While tubular segment 3 can be any tubular section of material suitable in composition and dimensions for petroleum well use, in one embodiment, tubular segment 3 may be conventional well casing or production tubing, such as ID 4.5", 5", 5.5", 6.625", 7", 8.625", 9.625", etc. In certain embodiments, the tubular segment includes an outer surface having at least one convex or concave section (including convex and concave sections on same tubular segment) to modify the direction of propellant expansion. As one example, the concave or convex portion may have a height of 0.25 inches and a length of between 6 and 8 feet, i.e., a radius of curvature between about 215 feet and about 385 feet. Other embodiments could employ radii of curvature between 50 feet and 700 feet (or any sub-range there between) or radii of curvature outside that range. The detail of FIG. 2 illustrates an exaggerated concave surface with a radius of curvature "R."

Positioned on an outer surface of tubular segment 3 is a propellant containment structure 10. In the illustrated embodiment, containment structure 10 is a concentric sleeve 11 positioned over tubular segment 3 and creates an annular volume which will enclose the propellant and in certain alternative embodiments, other well stimulation materials. Concentric sleeve 11 may be constructed of enumerable materials suitable for a wellbore environment. In many embodiments, it is preferable that concentric sleeve 11 be formed of a material that will maintain its integrity under normal wellbore conditions, but will disintegrate or rapidly degrade once the propellant material is ignited (or alternatively degrade over a designated time period). Non-limiting examples of such materials include high strength polymers, carbon fiber composite materials, carbon fiber weave with energetic materials embedded therein, flammable epoxy compounds, or metals that will decompose under the heat and pressure of the ignited propellant (e.g., titanium, magnesium). Alternatively, concentric sleeve 11 could be formed of ported steel sheeting with the ports providing an exhaust path for the gases produced by the burning propellant. The ports in the steel sheeting could also take on a specific pattern configured to direct the force of the gases in a particular direction. In certain embodiments, the sleeve 11 could be formed of a polymer shell wall and the polymer shell wall include at least one internal pocket containing an agent for dissolving the polymer. Typically, these pockets would have a lining resistant to the dissolving agent, but detonation of the propellant ruptures the internal pocket(s) and brings the dissolving agent into contact with the polymer.

Although FIG. 2 illustrates a concentric sleeve 11 as the propellant containment structure, the propellant containment structure may be formed of separate structures running along the length of tubular segment 3 and spaced around the circumference of tubular segment 3. Typically, such separate containment structures would be spaced evenly around the total circumference of tubular segment 3 to generate a roughly equal pressure wave in all directions when the propellant is ignited. However, there may be particular applications where the separate containment structures are not evenly distributed around the tubular segment circumference in order to direct the pressure wave in less than all directions.

In the FIG. 2 embodiment, there is shown at least one burst disc, and more preferably a plurality of burst discs 30 positioned along the tubular segment. The "burst" or "rupture" discs are conventional non-reclosing pressure relief devices that are a type of sacrificial part because they have a one-time-use membrane which fails at a predetermined differential pressure. The membrane is usually made out of metal, but nearly any material (or different materials in layers) can be used to suit a particular application. In preferred embodiments, the burst discs will be selected to rupture at or below a peak pressure produced when the propellant is ignited. In some embodiments, the plurality of burst discs will be selected to fail at the same pressure. In other embodiments, the burst discs may be selected to fail at different pressures. A nonlimiting example of a suitable burst disc is the P series conventional rupture disk having a failure pressure somewhere between 500 and 11,000 psi (e.g., 1,000 psi, 5000 psi, 9,000 psi, etc.) available from Fike Corporation of Blue Springs, Mo. However, other embodiments may employ bust discs which have higher operating ranges.

As suggested in FIG. 2, the failing of the burst disc will open a passage between the interior and exterior of tubular segment 3. The embodiment of FIG. 2 also illustrates a valve 20 which is capable of isolating the burst disc (or the aperture caused by the failing burst disc) from the interior of tubular segment 3. In this embodiment, valve 20 is formed by sliding sleeve 21, but other non-sleeve valve configurations could be used in other embodiments and still further embodiments may have no valve whatsoever. The sleeve in FIG. 2 is shown as covering only one burst disc 30, but in other embodiments the sleeve may be long enough to cover all burst discs. The FIG. 2 embodiment may include a series of shear pins (not shown) holding sleeve 21 in place until sufficient force acts on sleeve 21 to shear the shear the pins. The requisite force for moving sliding sleeve 21 may be applied by any conventional (or future developed) means, for example a mechanical opening tool on coil tubing or a ball or wiper plug seating on the top of sleeve 21 and hydraulic pressure being applied above the ball or plug.

As used herein, "propellant" means any energetic material, including high and low order explosives, composite propellants, extruded composite propellants, and aluminized composite propellants (e.g., isocynate cured HTPB with perchlorates), and deflagarants (i.e., substances which combust at a subsonic rate). Nonlimiting examples may include PETN, TNT, mixtures thereof, nitrates, perchlorates, mixtures thereof, explosives such as 3,3'-diamino-4,4'-azoxyfurazan (DAAF), and fire resistant, shock resistant insensitive high explosives (IHE) such as triaminotrinitrobenzene (TATB) or various insensitive explosive mixtures, or plastic/polymer-bonded explosives, which are similar to reactive materials. One family of composite propellants would be those formed from about 70% ammonium perchlorate with remaining percentages of HTPB, aluminum powder, and methylene diphenyl-diisocyanate (MDI). In certain embodiments, the propellant has a detonation velocity of between about 3000 and about 10,000 ft/sec. However, other propellants may have burn velocities in the range of about 500 to 3000 ft/sec. Likewise, certain embodiments will utilize a weight of propellant to generate a peak pressure at a formation/tool interface of between about 500 and about 50,000 psi (or any sub-range there between).

Many embodiments will include some type of reagent (reacting compound) or well enhancement compound within the containment structure as part of the propellant. Non-limiting examples of enhancement compounds include (i) acids; (ii) surfactants; (iii) clay stabilizers; (iv) sand stabilizers; (v) abrasive etching compounds, and (vi) calcium inhibitors. FIG. 2 illustrates a sleeve 11 containing alternative sub-compartments of enhancement compound 13 and propellant 16.

The embodiment illustrated in FIG. 2 shows a detonation cord 43 along the length of the containment structure which acts to ignite (or detonate) the propellant. Alternatively, an "activation rod" (or "igniter") of high temperature burning metal (magnesium or titanium) may run the length (or most of the length) of the containment structure. This detonation cord or activation rod is itself activated by a pressure activated firing mechanism 40. In some embodiments, the combination of an igniter and detonator may be required to produce the desired results, i.e., first activating the igniter and very shortly thereafter activating the detonator. In a particular embodiment, the firing mechanism includes a firing pin and is armed for activation by displacement of a sliding sleeve which is initially insulating the firing mechanism from significant pressure changes.

Those skilled in the art will recognize various methods in which the tool shown in FIG. 2 may be used to stimulate or otherwise treat a hydrocarbon production zone. One method generally comprises first running the stimulation tool into a wellbore formed through the formation as suggested in FIG. 1. The stimulation tool, or more commonly a series of stimulation tools, may be run in as segments of the casing string or as part of another tubular string (e.g., production tubing). In many embodiments, the stimulation tools are cemented in place along with the casing or other tubular string as part of a conventional cementing process. However, in other embodiments (e.g., open wellbore operations), the tubular string (and thus the stimulation tools) need not be cemented place.

In one example method (a manually fired "toe sub" method), the stimulation tool would be run near the end of the long string and positioned in the toe of a horizontal lateral wellbore and cemented in place. This "toe sub" may be the only propellant string in the tool or other propellant tools could be positioned in zones above the "toe sub." A wiper plug is pumped downhole during the cementing stage to engage and shift the sliding sleeve (such as sleeve 21 in FIG. 2) which had been acting as a protective sleeve to prevent accidental detonation through unintentional exposure of the pressure operated firing mechanism of "head" 40. After the cement has set, the operator then applies hydraulic pressure within the casing to trip the firing pin at a set pressure and detonate/ignite the propellant/energetic material. Once the propellant/energetic material activates and expands, a series hoop stresses are created and the cement between the tool and the open hole begins to crack and/or turn to rubble. The burst disc(s) collapse at a set pressure and open apertures in the stimulation tool to allow production from the zone of interest. In a modified embodiment, the detonation/ignition may be achieved through pressure codes detected by a pressure sensor located in the lowest propellant tool. This propellant tool could be battery powered and include electronics/software configured to capture and decode pressure pulses which would trigger a firing command. The use of pressure pulses to initiate a firing command is most advantageous on the lowest or initial propellant tool, but could be used on other propellant tools on the string.

In the above method, the operator may utilize completion fluid within the tubular to affect the nature of the stress generated on the formation. For example, if completion fluid is in the tubular string at hydrostatic pressure when the propellant is ignited, gases escaping into the tubular string will tend to create one stress profile on the formation. Alternatively, completion fluid in the tubular string imparts a different pressure profile against/into the formation when the fluid is under positive pressure (e.g., a pressure greater than the hydrostatic pressure from the well depth alone). It will be understood that when the rupture discs burst, broken up cement fragments, debris from drilling damage and formation fragments may be initially forced inside the casing to some degree, being reduced to smaller pieces in the process, and then expelled from the casing by the rebounding pressure wave. The operator can then pump into the zone of interest to perform stimulation such as hydraulic fracturing or flow tests. This process should tend to provide stimulation into the reservoir past any damage created during drilling and completion operations.

Figure 3A:
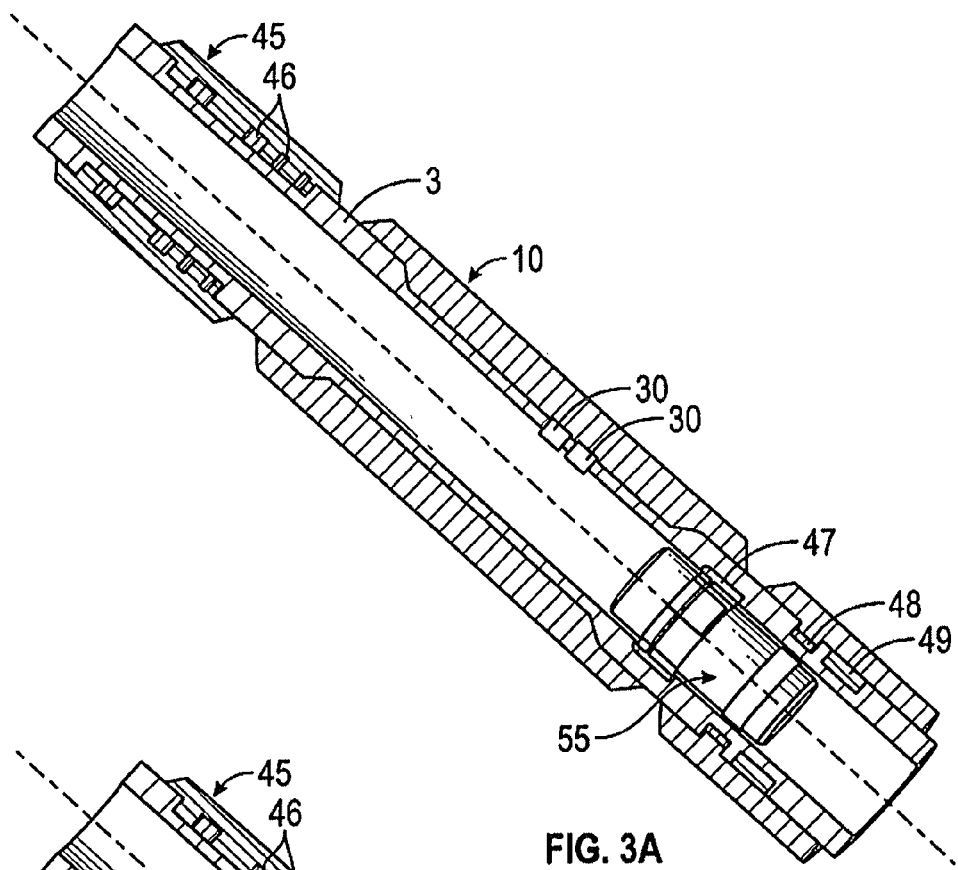
FIG. 3A is a cross-sectional view of a preferred stimulation tool embodiment of the present invention.

Another embodiment of the stimulation tool is seen in FIGS. 3A, 4A, and 4B. This embodiment provides a system for positioning a downhole tool at a specific location in a wellbore. As in the FIG. 2 embodiment, the stimulation tool 1 seen in FIG. 3A includes a tubular segment (or mandrel) 3 with a propellant containment structure 10 (also referred to herein as "propellant chamber" 10). The stimulation tool 1 will be incorporated into a tubular string positioned in a wellbore as suggested in FIG. 1. The details of propellant containment structure 10, the propellant (or energetic) materials and/or well enhancement compounds described in the FIG. 2 embodiment apply equally to the FIG. 3A embodiment, including a series of burst discs 30.

However, the FIG. 3A embodiment of stimulation tool 1 further includes at least one marker 45 (also referred to as a "tag" or "station ID") which has a code or identifier which can be read by a reader 58 in a plug (or other object or tool) traveling within the tubular segment 3. In the FIG. 3A embodiment, marker 45 is formed of a series of rings or bands 46 having different characteristics and where the arrangement of the rings 46 form the unique code. In this embodiment, the marker is formed with a unique identification code by using materials which exhibit different responses to eddy current measurements. The reader measures the eddy current effect in the casing and the markers. The eddy current effect is well understood by those skilled in the art, but may be described as follows. The reader emits energy which can be detected and invokes a response from the coded markers. In this case the reader emits electromagnetic radiation resulting in eddy currents in the markers, which are measured by eddy current sensors (which form part of the reader), as the energized reader travels along the length of the casing or other tubular member. Different materials in the coded markers exhibit different resistivity values.

In this embodiment, the resistivity difference due to the varying materials in the markers are determined by non-contact eddy current measurements techniques. As a result of sending a small amount of current (mA) into an eddy current sensor, a magnetic field and associated eddy current is induced. The reader will include at least one ring shaped eddy current sensor and an underlying eddy current ring shaped shield is placed either on the surface or embedded within the plug. This combination masks the sensing of eddy currents inside the plug and ensures that there is no interference in the measurement of either the magnetic field or resultant eddy current due to the presence of the plug.

The plug 55 (FIGS. 4A and 4B) will include a reader 58 and other electronics which allow plug 55 to identify marker 45 when plug 55 approaches or passes through marker 45. Thus, plug 55 will sometimes be referred to herein as a "smart" or "intelligent" plug. The details of this type of marker 45 and how it is detected by reader 58 is described in co-pending application Ser. No. 61/970,563, filed Mar. 26, 2014, which is incorporated by reference herein in its entirety. The marker locations in the tubular string are typically associated with some type of string feature or wellbore feature. For example, a marker may be positioned within a known distance from a valve sleeve, a landing nipple, or a stimulation tool, or the branching of a borehole casing. The marker may also utilized to reference known wellbore features such as the beginning of a particular geological formation, cemented vs. open hole sections, or horizontal vs. lateral sections of the wellbore. Typically, the markers are placed (e.g., cemented) in the wellbore and then the well is logged to determine the relative location of the markers and other wellbore features of interest. However, it may be the case the well is logged prior to insertions of the markers, and then the markers inserted into the wellbore to match the location of known wellbore features. In some cases, a well log such as a gamma-ray log or porosity log may be run to identify changes in the rock structure and identify wellbore areas of particular promise for stimulation. Once the primary stimulation is performed with the above described propellant tools and possibly hydraulic fracturing, the operator may choose to return at a later date, and through existing diagnostic logs, find areas that have not been produced and perform "secondary" stimulation. The well marker can then be used as a reference point for service tools that can locate the relevant components (e.g., sleeves) and perform the necessary operations (e.g., perforate/stimulate the contemplated new zone).

The embodiment of FIG. 3A illustrates "passive" markers, i.e., markers which do not emit a signal. However, other embodiments could employ active markers (e.g., RFID tag markers). It will be understood that when multiple tools 1 are positioned in a tubular string as suggested in FIG. 1, the markers 45 and reader 58 in plug 55 allows the plug 55 to identify the particular tool the plug is approaching and about to travel through. The FIG. 3A embodiment of stimulation tool 1 also includes latch profile 47, a hand-shake sensor 48, and an electronics module 49. As seen in FIGS. 4A and 4B, the plug 55 includes a deployable latch key 59, and expandable seal 57, electronics chamber 56, and battery space 60. As plug 55 travels through the tubular string, its reader 58 will detect marker 45 and the onboard electronics will cause latch key 59 to activate in a position such that latch key 59 will engage with latch profile 47. In one embodiment, plug 55 travels down the tubular string with latch key 59 deployed outward, but is able to flex inward as it passes various latch profiles and other profiles. When plug 55 detects (e.g., reads, decodes, and initiates a command) the appropriate marker 45, the latch key 59 is activated by being locked in an extended position such that plug 55 seats in the next latch profile it encounters (a more detailed embodiment of this is described below in reference to FIGS. 7A and 7B). When plug 55 seats in the appropriate latch profile, the plug's electronics may carry out various programming, such as setting expanding seal 57. Likewise, hand-shake sensor 48 will confirm the presence of plug 55 and indicate that electronics module 49 should carry out its programming. In one embodiment, the stimulation tool's electronic module will initiate ignition of the propellant in chamber 10 once the plug 55 has been seated. In certain embodiments, plug 55 will transfer the power to stimulation tool 1 having a passive detonator and thus provide the power needed to ignite the propellant. Power from plug 55 can also be used to operate accessory components on stimulation tool 1, e.g., temperature and pressure transducers. In one embodiment, the circuitry adapted to transfer electrical power includes induction coils in the stimulation tool and in the plug 55.

Other embodiments could include additional sensors on the plug's electronics card. These sensors may include magnetic compasses, inclinometers, accelerometers, and other directional measuring devices, which would be advantageous when directional stimulation is desirable as described in more detail below.

Figure 8A:
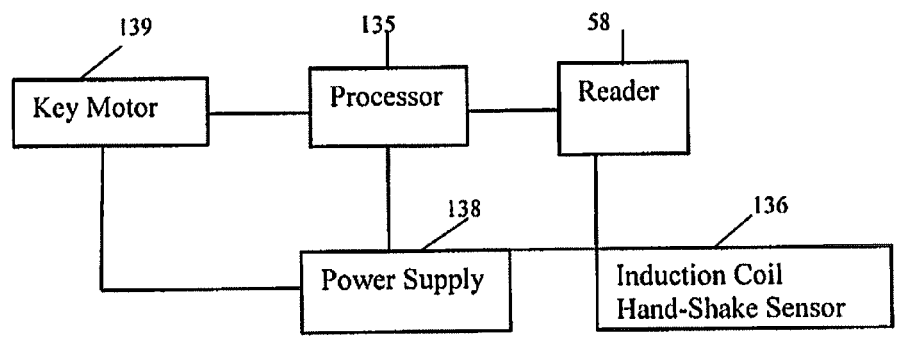
FIGS. 8A to 8C illustrate diagrams of electronic components used in certain embodiments.

FIG. 8A is a diagram of electrical components associated with this embodiment of plug 55. Plug 55 will include a controller (e.g., the processor 135) which communicates with reader 58, key motor 139 and is powered by power supply (e.g., batteries) 138. The power supply 138 may optionally power the induction coils 136 which may be used to transfer power to any electronics (or electrically powered components) embedded within the tubular string tool. Alternatively, direct electrical contacts may alternatively transmit power between the plug and the components within tubular string tool. The key motor 139 would deploy keys as described above or a similar motor could be used to deploy an active sealing element (as described below).

Figure 8B:
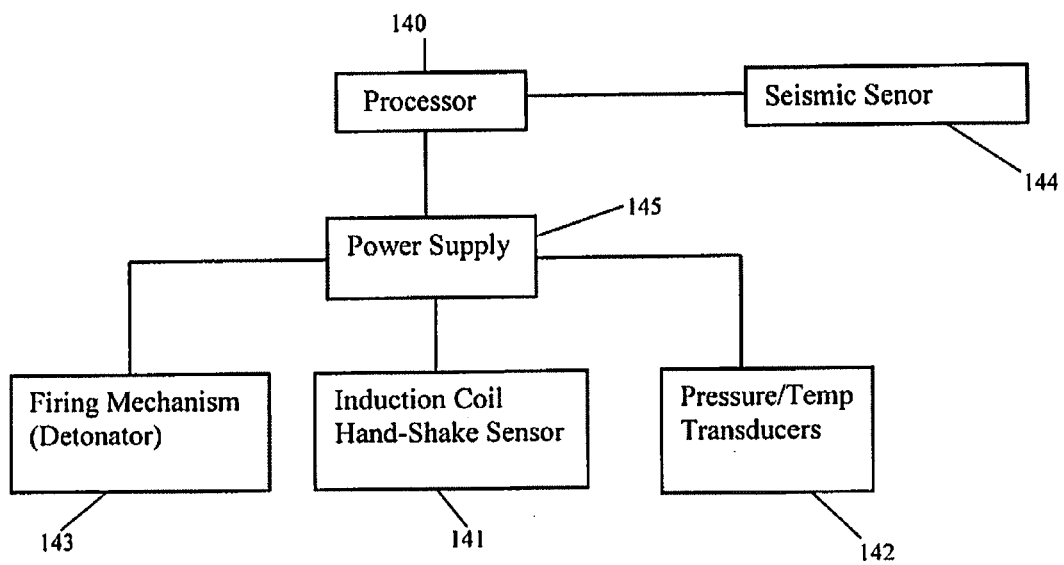

In certain embodiments, the propellant tool forming part of the tubular string will have embedded electronic components as suggested in FIG. 8B. The propellant tool may have the induction coils 141 which receives power from the plug induction coils 136. In certain embodiments, the transfer of power across the induction coils will be viewed as a hand-shake signal between the plug 55 and the propellant tool. However, in other embodiments, the hand-shake sensor may be separate circuitry. The power received by the induction coils may be used to activate the firing mechanism (detonator) 143. There will also be embodiments where the circuitry associated with the propellant tool will have its own power supply, e.g., batteries, as opposed to receiving power from plug 55. Thus, the "power supply" 145 in FIG. 8B (and other Figures) may include batteries and the DC-DC converter/regulator needed to convert voltage from batteries to the levels require by processors and other sensitive electronics.

In all embodiments described here, the firing mechanism may be an igniter (e.g., a device generating high temperatures, but not a significant pressure or shock wave) or a detonator (e.g., a device generating heat and a significant shock wave, for example, a blasting cap). In certain embodiments, the firing mechanism may include both a igniter and a detonator (e.g., the initial ignition of the propellant/explosive by the igniter followed by detonation via the detonator). Although not all embodiments of the propellant tool will require a controller or processor, certain embodiments may have a processor 140 to provide more control of firing the propellant or operating sensor devices (e.g., temperature and/or pressure transducers 142) embedded with the propellant tool. Alternatively, a seismic sensor 144 (FIG. 8B) could be incorporated into the control circuitry. The processor may be programmed to read a coded series of pressure pulses detected by the pressure transducer and then issue certain commands, e.g., such as activating the firing mechanism. Likewise, the processor could interpret signals received from the seismic sensor which has detected seismic waves generated at the surface and then activate the firing mechanism (or issue other commands). All of temperature sensors, pressure sensors, timers, and seismic sensors (and sensors for detecting other conditions) may be referred to as "event sensors." The processor detecting signals from one or more of these events can be programmed to activate the firing mechanism or issue control instructions to other circuit components. Those skilled in the art will recognize that FIGS. 8A to 8C are merely illustrative examples of electronic component configurations which could be used in the embodiments described herein and many other electronic configurations could be employed in the alternative.

Figure 3B:
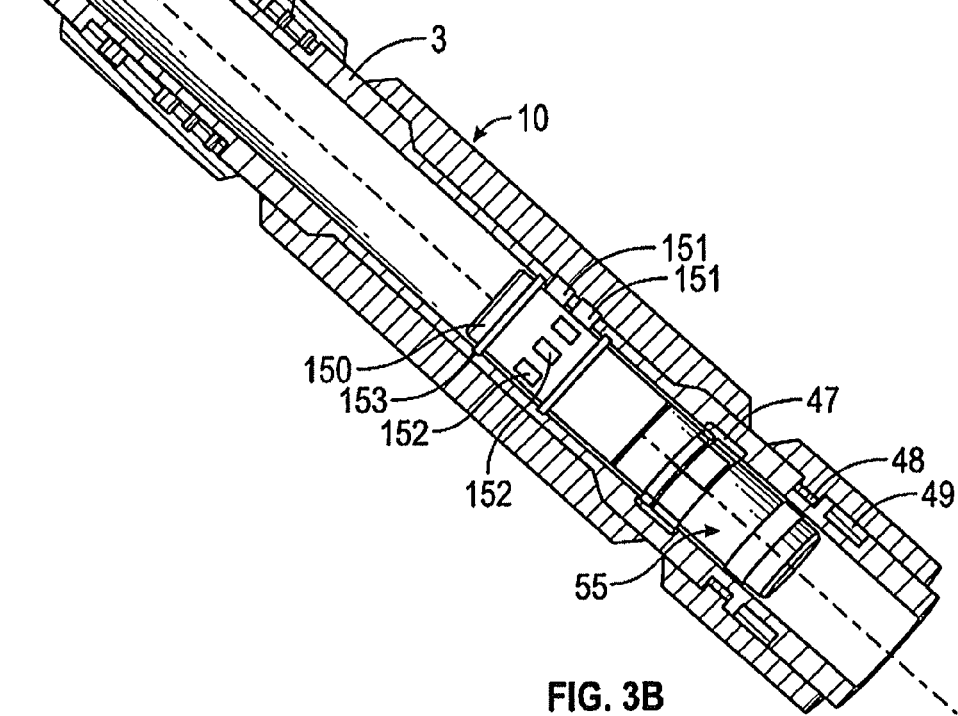
FIG. 3B is a cross-sectional view of another stimulation tool embodiment of the present invention.

FIG. 3B suggests another embodiment of a stimulation tool. In FIG. 3B, activation plug 55 further includes a propellant containing canister 150 connected to the activation plug. Provided canister 150 has a small enough outer diameter to travel through the tubular string, its other dimensions can vary considerably. The general purpose of canister 150 is to carry additional propellant to supplement the effect of propellant in propellant chamber 10, so the length of canister 10 is governed by the mass of additional propellant desired to be positioned adjacent to a chamber 10. This example of canister 150 shows a series ports 152 positioned around the circumference of canister 150. The ports 152 provide an outlet for expanding gases when the propellant within the canister is ignited. In a preferred embodiment, ports 152 are weakened sections of the canister wall, but could also be a low pressure burst discs. Canister 150 may also include seals 153 on each side of ports 152. Although not explicitly shown, higher tolerance inner diameter seal bores could be formed on the inner surface of tubular segment 3 at the location where the sealing effect is desired. Seals 153 could be of many different types, with one example being conventional pressure activated chevron seals. The chevron seals would be oriented such that the expanding gas from the propellant activates the seals which then block the gas from escaping beyond the seals into the tubular string (i.e., directing the gas through ruptured burst discs 151 as described below). The FIG. 3B embodiment shows the tubular string segment 3 having a series of burst discs 151 positioned in the wall of the tubular. The respective lengths of canister 150 and plug 55 will be configured such that when plug 55 has landed in the latch profile 47, ports 152 are positioned under (or adjacent to) at least one burst disc 151 with seals 153 bracketing the ports 152 and burst discs 151. In one embodiment, it is contemplated that the ignition of propellant in propellant chamber 10 will collapse burst discs 151 and any material covering port 152, thereby igniting propellant in canister 150. Alternatively, a separate igniter or detonator could be positioned within canister 150 and the igniter or detonator activated by the control circuitry of plug 55. Although not illustrated in the Figures, an alternative canister 150 could have a single port 152 and be rotatively connected to plug 55. As described in reference to FIG. 4C below, an orienting motor 66 positioned in plug 55 would project a positioning shaft 65 into canister 150 with canister 150 rigidly fixed to positioning shaft 65. An orientating sensor associated with plug 55 (as explain in more detail below with respect to FIG. 8C) would determine the orientation of canister 150 and provide the data necessary for orientating motor 66 to align port 152 with burst discs 151.

An alternative embodiment of intelligent plug 55 is seen in FIG. 4C. This version of plug 55 will include a perforating gun 63 connected to the plug. As used herein, "perforating gun" means any type of explosive mechanism configured to perforate casing or other tubular members within a wellbore. In this embodiment, perforating gun 63 includes a cylindrical gun body 64 rotatively positioned on plug 55. An orientating motor 66 positioned within plug 55 will project the positioning shaft 65 into gun body 64 with body 64 rigidly fixed to positioning shaft 65. In the FIG. 4C embodiment, a series of shaped, high-explosive charges 67 are positioned in gun body 64, with the charges oriented to direct explosive force radially outward. The charges are positioned generally inline along the length of gun body 64 in order that the explosive force is directed in a narrow "arc" relative to a cross-section of the borehole. For example, if a transverse cross-section through body 64 is visualized, the force of shaped charges 67 is directed in the 12 o'clock direction and (depending on the geometry of the charges) will transmit the explosive force in an arc approximately 10° to 20° on either side of the 12 o'clock position. Thus, it will be understood that the orientating motor 66 can rotate gun body 64 in any direction in order to selectively direct the explosive force of shape charges 67 in that direction. FIG. 4C also shows an anti-rotation spline 68 projecting upward from latch key 59. Anti-rotation spline 68 will engage a mating anti-rotation groove (not illustrated) formed in a the latch profiles 47. This insures the rotative orientation of plug 55 is fixed after landing and that all rotation of orientation motor 66 translates to relative rotation of perforating gun body 64.

Figure 8C:
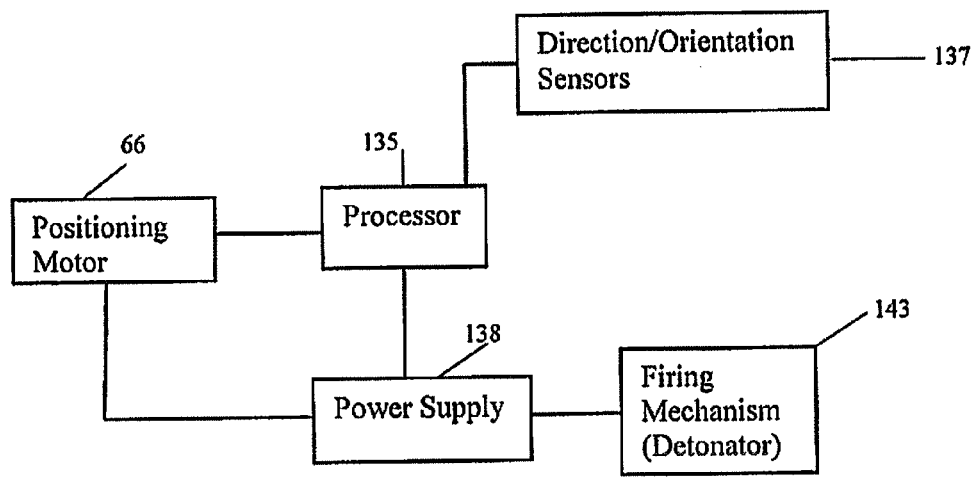

FIG. 8C illustrates one circuit which could be employed with the FIG. 4C intelligent plug. An orientation sensor 137 will be positioned within plug 55 (or alternatively gun body 64). In certain embodiments, the orientation sensor can be one or more of an accelerometer, an inclinometer, a compass, a gyroscope, a magnetometer; and an inertial measurement unit. The orientation sensor will be able to detect the rotative orientation of plug 55 once it has landed in latch profile 47. With data indicating the landed orientation of plug 55 and the "upward" direction (i.e., the direction opposite the direction of gravitational force), processor 135 may operate positioning motor 66 (via power supply 138) to rotate the gun body 64 in the orientation for which the explosive force of the shaped charges are intended to be directed. Processor 135 can then provide the firing command to active firing mechanism 143 which detonates the shaped charges in the perforating gun.

Figure 5:
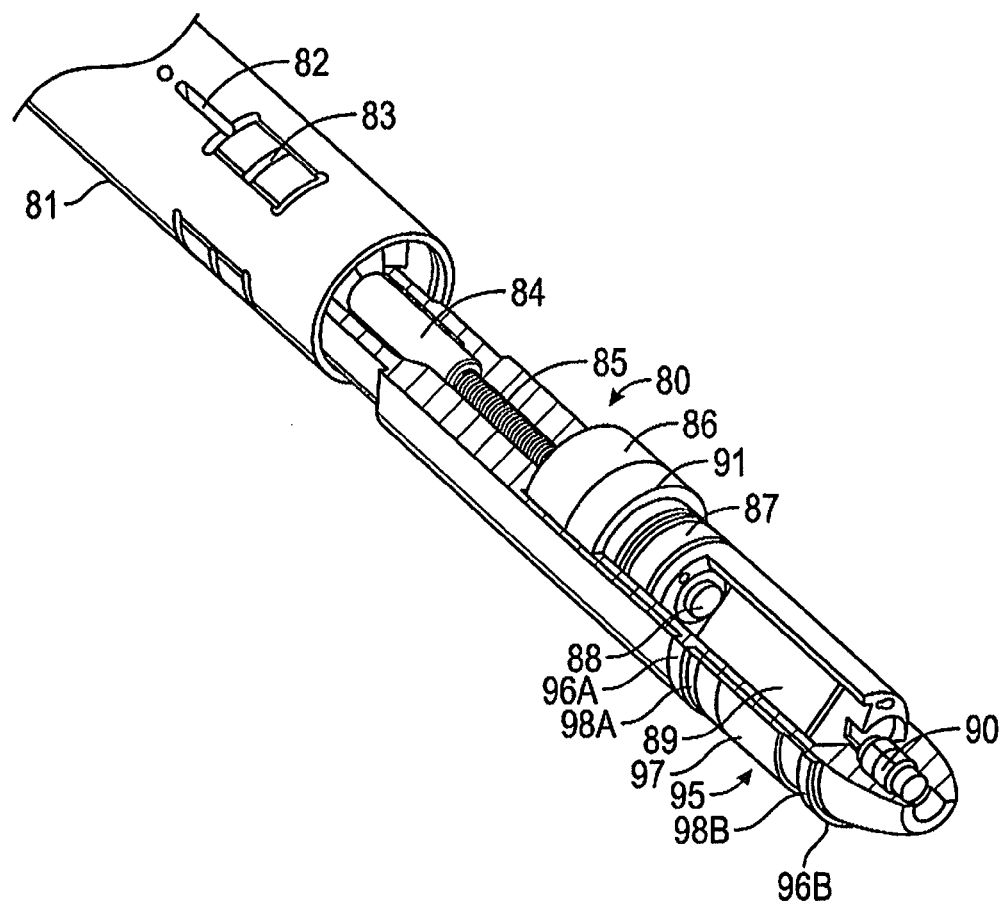
FIG. 5 illustrates a tethered downhole tool embodiment of the present invention.

FIG. 5 illustrates a further embodiment of the present invention. This embodiment is a downhole tool 80 which incorporates a reader as described above and which performs a specified function based upon the reader detecting a specific marker in the wellbore. In the FIG. 5 embodiment, the function is the activation of a "profile key" (or simply "key") to engage a profile (sometimes referred to as a "latch profile") formed on the inside of the tubular string through which the tool is traveling (e.g., latch profile 47 seen in FIG. 3). The "key" can be virtually any structure extending from the tool body which is capable of engaging a profile on the tubular string and securing the tool at a location associated with the profile.

There are any number of functions which could be performed by the downhole tool. The function of the downhole tool could simply be to engage a latch profile which is formed on a sliding sleeve in order to allow the sleeve to be moved as part of another mechanism (e.g., uncovering a flow port of a valve or uncovering a pressure activated firing mechanism). The tool may also include other components which perform other actions once the key fixes the overall tool at a particular location. For example, the tool may include expanding seals that form a seal in the wellbore at the location of the tool, or the tool may include measuring and/or recording equipment which measures and/or records conditions (e.g., time, pressure, temperature, and resistivity) at that location in the wellbore.

In the FIG. 5 embodiment, the tool 80 includes a connector body/lock housing 81 which encloses the extendable key 83. In the FIG. 5 embodiment, connector body/lock housing 81 is adapted to connect with some type of "tether" extending from the wellbore surface. For example, the tether could be wire-line, slick-line, coiled tubing, jointed piping or any other conventional or future developed methods for tethering tools which are then lowered into the wellbore from the surface using the tether. As explained below, other embodiments may likewise be "untethered." In FIG. 5, a spring provides force to push the keys out. The spring vent (or slot) 82 allows space for the spring to expand past the inner diameter of the body and into the slot to keep force on the key. FIG. 5 illustrates one electro-mechanical mechanism for activating the key 83, which includes activation tube 84, threaded activation rod 85, upper magnetic clutch element 86, lower magnetic clutch element 91, and electric motor 88. Upper and lower magnetic clutch elements are simply magnets in the illustrated embodiment. Although not shown in FIG. 5, a sealed partition exists between the magnets in order to effectively seal the electronics of the tool from wellbore fluid that will come into contact with the mechanical elements. The rotation of lower magnetic clutch element 91 by motor 88 transfers torque across the sealed partition to upper magnetic clutch element 86, which in turn is connected to and transfers torque to threaded actuation rod 85, activation tube 84, and ultimately mechanical elements associated with key 83. The activation tube 84 has a taper or cone which forces the key outward while springs bias the key inward. Likewise, movement of the activation tube and the cone out of the way of the key allows the key to retract.

Located in the lower end of tool 80 are electronics housing 87, electronics card 89, and battery 90 for powering the electronics and motor. In the illustrated embodiment, the electronics housing will include circuitry associated with a marker (or tag) reader as described above. The electronics card 89 will include the controller (e.g., microprocessor) receiving information, processing software steps, and generating the instructions to operate the reader, motor, and other functions the particular tool may have. For example, in the tool of FIG. 5, the tool 80 includes the seal assembly 95 formed of a main seal member 97, backup seal members 98, and centralizing rings 96. In this example of seal assembly 95, main seal member 97 is a fixed position seal which is sized to engage a narrowed diameter seal bore section of the tubular string in which the tool travels. The centralizing rings act to concentrically align the seals within the seal bore and the backup seals provide additional sealing capacity in the event the main seal member fails. However, in other embodiments, seal assembly could be an active seal which expands from the tool body in order to form the seal with the tubular string in which the tool travels (i.e., a sealbore within the string is not required). The controller described above would provide the commands to activate the expanding seal in this latter example.

Figure 6:
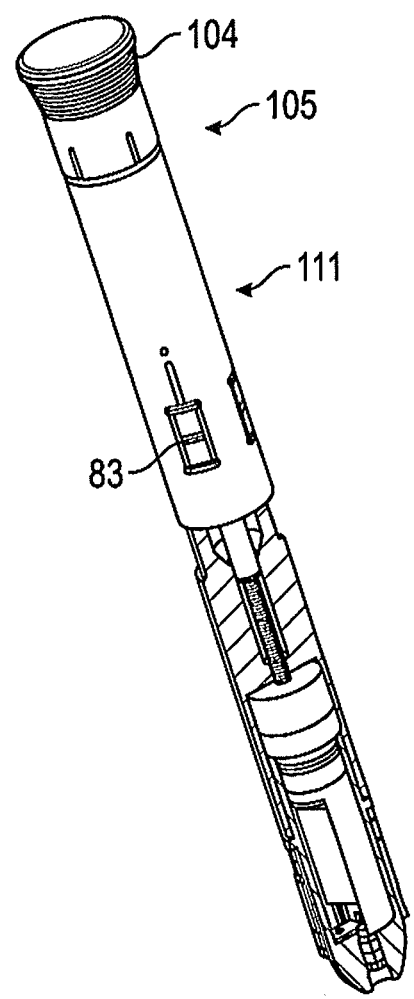
FIG. 6 illustrates an untethered downhole tool of the present invention.

FIG. 6 illustrates an embodiment of tool 80 similar to that of FIG. 5, but in FIG. 6, the tool 8 does not have the connecting body 81 for tethering of the tool to the wellbore surface. Rather FIG. 6 illustrates an untethered embodiment where the tool travels downhole without a connection to the surface. In FIG. 6, the tool includes the flexible cup 104 which, in response to fluid pressure induced in the tubular string above the tool, provides an expanded surface for the fluid to act against and increases the force propelling the tool downhole. Naturally other untethered embodiments not using the flexible cup 104 are possible, for example embodiments relying primarily on gravity to move the tool downhole. Likewise, certain embodiments of the tool may be buoyant in particular drilling fluids and will be initially pumped downhole, but then are capable of "floating" to the surface after pumping pressure is removed.

Figure 7A:
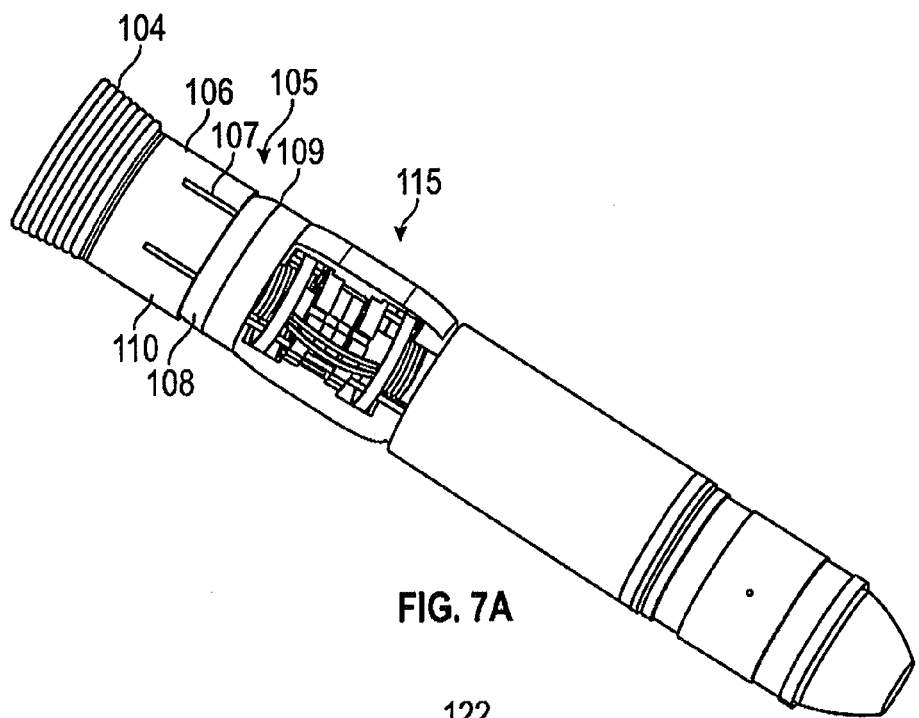
FIGS. 7A and 7B illustrate a drag block embodiment of the present invention.
Figure 7B:
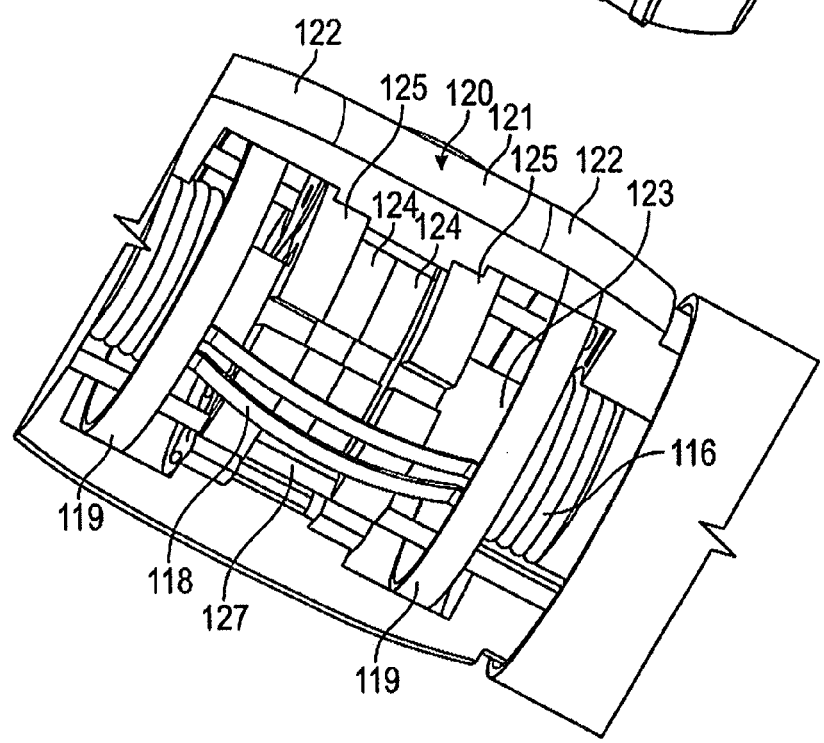

FIGS. 7A and 7B illustrate another embodiment of tool 80 which includes a "drag block" type of key. FIG. 7B is a cutaway section illustrating drag block assembly 115 in more detail. The assembly 115 includes the drag block or drag key 120 which is formed of the main key section 121 and the ramp sections 122 formed on each side of main key section 121. A series of drag block keys 120 are formed around the circumference of tool 80. A series of ring members underlying drag block keys 120, bottom out rings 124 and lockout rings 125, will be positioned on the central axis rod 123. The anti-rotation keys or rods 127 hold the lock rings steady forcing them to follow the thread pattern of the central rod and move to the center of the mechanism. FIG. 7A shows lockout rings 125 in the final inward or locked position. When the lockout rings 125 move outward beyond the reach of the anti-rotation rod, they may then spin with the threaded central axis rod, but do not travel, preventing them from being rotated out. The tension springs 116 will provide torsional force to insure the lockout rings may rotate to their lock position as explained below. The drag block springs 118, secured in position by spring retainers 119, will act to bias the drag block keys 120 outward as explain below. It will be understood that a drag block spring 118 is positioned under each drag block key 120.

In operation, the tool 80 will move down the tubular string of the borehole by way of fluid pressure acting on the flexible cup 104. The main key sections 121 of drag block keys 120 extend sufficiently beyond the outer diameter of the housing of tool 80 such that main key sections 121 are biased against the internal wall of the tubular string by drag block strings 118. Thus, as the tool 80 moves down the tubular string, the main key sections 121 will "drag" on the internal wall of the tubular string. When tool 80 encounters latch profiles formed on the internal wall of the tubular string (e.g., the latch profiles form a wider ID than the rest of the tubular wall), the main key sections flex outwardly as urged by drag block springs 118. As the tool 80 moves out of the profile, the main key sections 121 will flex inwardly against drag block springs 118 (assisted by the ramp sections 122 first engaging the edges of the latch profiles at a reduced angle). At this time, the lockout rings 125 are rotated to the unlocked position (i.e., positioned outward of their position seen in FIG. 7B) and do not inhibit the inward movement of drag block keys 120. Thus, with sufficient fluid pressure acting on the flexible cup 104, the tool 80 will travel past latch profiles it encounters as long as drag block keys 120 may flex inwardly. When it is desirable for tool 80 to engage a particular latch profile (the "target" latch profile) and remain locked into the target latch profile, the tool controller will issue a command releasing torsion springs 116 to rotate lockout rings into the lock position as the tool 80 moves within the target latch profile. Thus, when the drag block keys move outward in the target latch profile, they can no longer flex inward and will become locked in the target profile. It will be understood that tool 80 includes a reader which reads markers associated with the latch profiles, thereby allowing the controller to recognize when the target latch profile is approaching and when the lockout rings must be rotated to the lock position. In one example, the drag block keys engage the tubular string inner surface for its entire travel path through the string. However, in other examples, the drag block keys may initially be retracted, and only deploy at a later point in its travel (typically based upon detecting a particular marker).

FIG. 7A also suggests how this embodiment includes the flexible cup 104 which functions as described above and further operates in conjunction with the expandable seal assembly 105. The expandable seal assembly 105 is formed of expandable seal member 106, having expansion slots 107 which operate on outwardly inclined expansion surface 108. Once the tool 80 has become locked into the target latch profile as described above, pressure acting on flexible cup 104 will exert increasing force on expandable seal member 106. With sufficient force, expandable seal member 106 is forced to move down expansion surface 108 which causes the expansion slots 107 between seal fingers 110 to widen. With the spreading of the individual seal fingers 110, expandable seal member 106 engages the inner surface of the tubular string as the seal fingers (and the upper end of slots 107) move over seal stop 109.

In one example of this seal, a mild steel structure has an elastomeric material molded to it. A piece between the top of the seal and the top of the split area is designed to bend and conform to the inner diameter. An o-ring inside the top of the expandable seal seals the inner diameter. Alternatively, a standard rubber seal, like a packer element seal, may be employed. The rubber cup will provide downward force after the keys seat and a lock ring inside the seal will maintain the force.

Figure 9:
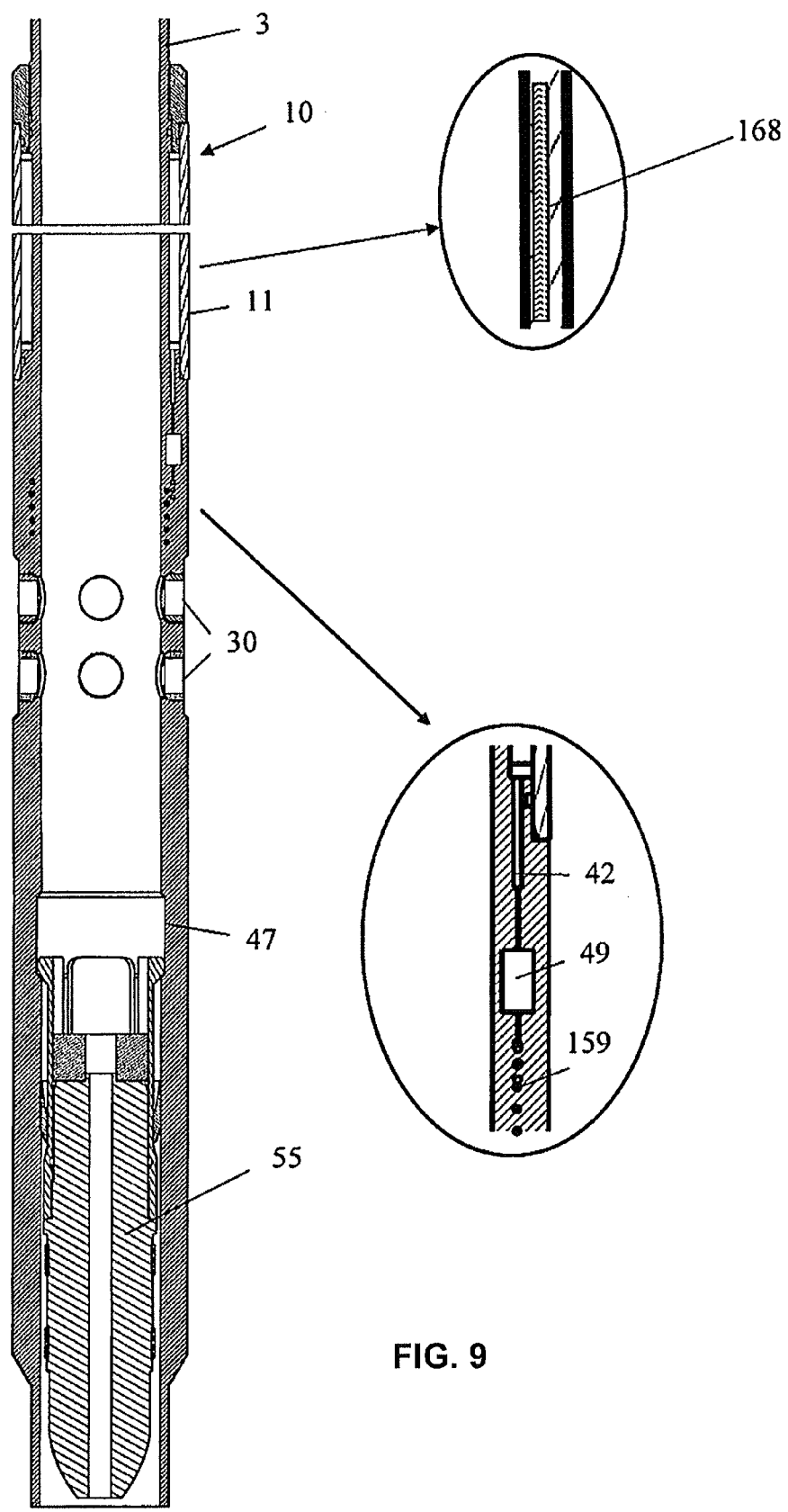
FIG. 9 illustrates modified stimulation tool embodiment utilizing an intelligent plug.

FIGS. 9 through 12 illustrate another embodiment of the propellant tool, system, and method described above. FIG. 9 shows a version of stimulation tool 1 including tubular segment 3 with the propellant containment structure 10 formed of concentric sleeve 11 (it being understood that FIG. 9 shows the propellant containment structure 10 truncated). FIG. 9 includes a series of burst discs 30, but these burst discs are not positioned under the concentric sleeve 11 as in earlier embodiments. FIG. 9 shows an intelligent plug 55 (also referred to as an "activation plug") landed in latch profile 47. One detail inset of FIG. 9 illustrates how this embodiment will have an electronics module/card (including batteries not shown) positioned within the wall of tubular segment 3 which is capable of activating a firing mechanism for igniting the propellant, e.g., igniter 42 (the electronics, battery, and firing mechanism forming one embodiment of what is sometimes referred to as the "propellant ignition circuit"). Of course, the firing mechanism could alternatively be a detonator or a combination of an igniter and detonator. An induction coil 159 will also be positioned in the wall of the tubular segment and connected to electronics module 49 such that the module is capable of sensing a current (or other changes in electrical properties) created in induction coil 159. Although not shown in FIG. 9, this embodiment may include a coded marker positioned uphole of propellant containment structure 10.

FIGS. 10 to 12 illustrate more details of intelligent plug 55. The rear section of plug 55 will include collet fingers 162 which are constructed to flex inward in one state and resist flexure in a second state, as explained in more detail below. Plug 55 may also include a series of induction coils 160 formed on its exterior surface which will communicate with an electronics card 89 and battery power supply 90 positioned within the interior of plug 55. Reader 58 will likewise communicate with electronics card 89. FIG. 11B also suggests how an electric motor 88 within plug 55 is powered and controlled by electronics card 89 and power supply 90. Motor 88 will provide torque to magnetic clutch 165 which in turn will transmit torque to locking arm 164. As described above, magnetic clutch 165 operates to transmit torque across a fluid-tight boundary so that while locking arm 164 is exposed to wellbore fluids, the interior of plug 55 is not.

FIGS. 10 to 12 also illustrate a seal (in this embodiment cup seal 170) formed on the outer surface of plug 55 which will operate to engage and seal against the inner wall of the tubular segment. In certain embodiments, the body of plug 55 may be formed of a dissolvable material and sealed solvent chambers 168 contain a solvent (dissolving agent) capable of substantially dissolving the material forming the plug body when the chambers 168 are ruptured and release the solvent. One insert of FIG. 9 illustrates how certain embodiments of sleeve 11 could also include a chamber 168 which could contain an agent, that when released, tends to dissolve (or alternatively help combust) the material of sleeve 11.

FIGS. 11A and 11B show collet fingers 162 in a first state where they may flex inward. Thus, as plug 55 travels down tubular members within the wellbore, including the tubular segments of the propellant tools, the outwardly projecting collet tips 163 on collet fingers 162 will drag along the interior tubular walls. In this state, the collet tips may expand into latch profiles 47 (seen in FIG. 9), but will flex inward and out of the latch profiles as pump-induced fluid pressure above plug 55 moves the plug downhole. As specifically seen in FIG. 11A, the locking arm 164 is rotated to a position where it does not interfere with the inward flexure of collet tips 163. However, when electronics on card 89 sense one or more preprogrammed conditions, motor 88 will be powered to transmit torque, via magnetic clutch 165, to locking arm 164. As locking arm 164 moves to a second position to block the inward flexure of collet tips 163 (seen in FIG. 12A), plug 55 transitions to a second state where the collet tips 163 will now remain ("land") in a latch profile and not be displaced from the latch profile by uphole fluid pressure. Naturally, the collet fingers 162, locking arm 164, and motor 88 are simply one example of a "latch mechanism" which could be used in conjunction with plug 55 and any other conventional or future developed latch mechanism for selectively engaging latch profiles could be employed.

One mode or method for employing this embodiment of propellant tool 1 and intelligent plug 55 may be envisioned with respect FIG. 9. Plug 55 will be pump through a series of propellant tools 1 positioned within a wellbore as described previously. At this point, plug 55 is in the state where collet fingers 152 may flex inward, thus the plug will pass through and not land in any latch profiles it encounters. As plug 55 approaches the coded markers (not shown) associated with each propellant tool, the reader 58 detects the markers and reports the marker's code to the controller on the electronics card. Likewise, the electronics and power supply may energize the induction coils 160 on intelligent plug 55 as it travels downhole. Thus, a current may be generated in the induction coils 159 of the propellant tools 1 as the plug 55 passes the propellant tool and this condition serve as a signal to the tools' electronics modules that the plug has travelled past. This detection of the plug 55 passing induction coils 159 is one example of the propellant tool electronics receiving a "wireless" signal from plug 55 and the plug's electronics and induction coils 159 form one example of a wireless signal generator. Of course, other forms of a wireless signal (e.g., radio, sonic, or optical energy) could be alternatively employed.

When plug 55 detects the coded marker associated with the latch profile in which plug 55 has been programmed to land, motor 88 will begin moving locking arm 164 into the lock position where collet fingers 162 can no longer flex inward. It will be understood that while collet tips 163 are not in a latch profile, collet fingers 162 are slightly flexed inward and this prevents locking arm 164 from moving into its final lock position. However, torque from motor 88 is acting against locking arm 164 which creates a slight biasing force on collet fingers 162. When collet tips 163 encounter the approaching latch profile, they may then flex outward and allow locking arm 164 to move into its final lock position. Depending on the velocity at which plug 55 is traveling through the propellant tools, it may be advisable to have an extended length latch profile (e.g., 12" to 18") in order for locking arm 164 to have sufficient time to transition to its final lock position before the collet tips 163 can completely pass through the latch profile. Once in the latch profile, additional fluid pressure may be applied in order to set seal cup seal 170 and create a seal between plug 55 and the inner wall of tubular segment 3.

Another method embodiment is suggested in FIGS. 13A and 13B. FIG. 13A illustrates the vertical wellbore 200 with a deviated (e.g., horizontal) branch wellbore 201. Positioned within wellbore 201 is an outer tubular member (or "outer casing") 202, which in one nonlimiting example, may be 7" ID casing. The illustrated embodiment of outer casing 202 includes a plurality of propellant containing sleeves or "propellant sleeves" 207 similar to those described above. Each propellant sleeve 207 is illustrated as associated with a passive ID station as described above or other form of "coded marker" 205 and a latch profile 209. Naturally, in other embodiments not illustrated, multiple propellant sleeves may be associated with each marker and latch profile or vice versa. The FIG. 13A embodiment shows outer casing 202 being cemented into wellbore 201 by cement layer 203, but other embodiments could operate without outer casing 202 being cemented within the wellbore.

FIG. 13A suggests how an "intelligent plug" 215 similar to that described above will be pumped down into wellbore 201 (i.e., this plug 215 is untethered), detect coded marker 205, deploy keys 216, and engage latch profile 209. This embodiment of plug 215 includes a perforating gun 217 with a series of shaped charges 218 positioned to directed their explosive force over a comparatively narrow arc. As described above, the orientation of perforating gun 217 may be controlled by a motor in plug 218 and appropriate control circuitry, including an orientation sensor. The FIG. 13A embodiment will position latch profile 209 relative to propellant sleeve 207 such that when plug 215 lands in latch profile 209, the perforating gun 217 is in a position to fire through propellant sleeve 207. In certain embodiments, it is contemplated that shaped charges 218 firing through the propellant sleeve 207 will ignite the propellant therein. In other embodiments, a separate igniter and/or detonator as described in earlier embodiments may also act on the propellant.

FIG. 13A suggests one particular embodiment where one perforating gun 217 is directed upward to fire into the formation and another perforating gun 217 at a different location along the wellbore is directed downward to fire into the formation. As used in this context, "upward" means in a direction opposing the direction of gravitation force and "downward" means following the direction of gravitational force. In many embodiments, after the discharge of the perforating guns 217, the plug and perforating guns may be removed from the wellbore in any conventional or future developed manner. For example, plugs/perforating guns constructed of a drillable material may be drilled out, or alternatively those constructed of a dissolvable material may be removed with the appropriate solvent. A still further alternative constructs the plugs/perforating guns of a frangible material, such as a ceramic, which may be shattered by an impacting tool lowered downhole on coil tubing or by the force of the perforating gun detonation. The foregoing materials and methods of removal may apply to any of the intelligent plug devices described in this specification.

FIG. 13B illustrates a further method that may be performed in the wellbore 201 after the steps described in reference to FIG. 13A. FIG. 13B illustrates a plurality of inner tubular strings 220 positioned in wellbore 201. While FIG. 13B shows two strings 220A and 220B, other embodiments might include three or more strings. As one non-limiting example, inner strings 220 could be formed of 2⅜" (inner diameter) tubing. The inner tubular strings will have positioned along their length a series of multi-string packers 221 (dual string in FIG. 13B). These multi-string packers 221 allow the inner tubulars to communicate there through, but may be set in a manner to engage the inner walls of outer casing 202 and form a seal preventing fluid flow past the packers. In many embodiments, the packers 221 are designed to be "set" (expanded into their sealing state) by pressuring up on one the inner tubular members 220. The isolated section of outer casing 202 between two packers 221 may be referred to as "intervals" within the wellbore. Thus, FIG. 13B shows a first interval between packers 221A and 221B and a second interval between packers 221B and 221C. In many embodiments, the term "interval" will refer to different, packer isolated sections of outer casing 202 formed in a single geological zone of the wellbore (e.g., a "zone" being a section of the wellbore having substantially uniform geological formation characteristics). However, in other embodiments, different intervals may extend into or be co-extensive with different geological zones.

In the illustrated embodiment, each of the inner tubular strings 220 will have at least one valve 223 position on the string to allow selective fluid communication between the interior of tubular strings 220 and the interior of outer casing 202. The FIG. 13B embodiment shows inner string 220A with a valve 223A between packers 221A and 221B, while inner string 220B has a valve 223B between packers 221B and 221C. Other embodiments could have a different number of valves in each interval or conceivably, a valve(s) in one interval, but not in another. The valves 223 could be any conventional or future developed valves, but in one particular embodiment, are sliding sleeve valves having an internal latch profile on the sleeve component. In this embodiment, an opening tool could be run on coil tubing into each of the inner strings and the opening tool used to engage a valve's latch profile and shift the sleeve to an open position (or closed position if the sleeve is already in the open position).

In the FIG. 13B embodiment, valve 223A could be opened, allowing hydrocarbons 231 in the formation associated with the first interval (between packers 221A and 221B) to flow into outer casing 202 (through the apertures created by the perforating gun) and into valve 223A to be ultimately recovered at the surface. Simultaneously (or at different time), valve 223B could be opened and a pressurizing fluid (e.g., water) 232 pumped through inner string 220B into the second interval between packers 221B and 221C, and ultimately into the formation associated with this second interval. It will be understood that water 232 pumped into the formation at the second interval (presuming both intervals are in the same zone) will tend to maintain pressure across the zone as hydrocarbons are withdrawn.

Although the above specification has disclosed the invention in terms of certain specific embodiments, those skilled in the art will recognize many obvious modifications and variations. All such modifications and variations should be considered as falling within the scope of the following claims.

The invention claimed is:

1. A tubular string for positioning in a wellbore, the tubular string comprising:
   a. a plurality of markers positioned along the tubular string, the markers each including multiple passive elements arranged to create a distinct code readable as a reader passes through the tubular;
   b. a plurality of propellant chambers positioned on an outside surface of the tubular string, each propellant chamber being in the vicinity of at least one of the markers; and
   c. a propellant ignition circuit associated with each propellant chamber.

2. The tubular string according to claim 1, wherein the propellant chambers are annular sleeve structures formed around a section of the tubular string.

3. The tubular string according to claim 2, wherein the annular sleeve structures are formed of a material from the group consisting of a high strength polymer, a carbon fiber composite, and a ported steel sheeting.

4. The tubular string according to claim 1, wherein the ignition circuit is at least partially within an ignition housing positioned on an outer surface of the tubing string.

5. The tubular string according to claim 1, wherein the ignition circuit includes at least one of an igniter or detonator.

6. The tubular string according to claim 1, wherein the tubular string comprises a series of discrete tubular sections connected together.

7. The tubular string according to claim 1, further comprising induction coils to supply power to the ignition circuit.

8. A tubular string for positioning in a wellbore, the tubular string comprising:
   a. a plurality of markers positioned along the tubular string;
   b. a plurality of propellant chambers positioned on an outside surface of the tubular string, each propellant chamber being in the vicinity of at least one of the markers;
   c. a propellant ignition circuit associated with each propellant chamber;
   d. wherein an inner surface of the tubular string includes at least one latch profile associated with each propellant chamber, wherein the latch profile is configured to engage an activation plug traveling through the tubular string; and
   e. wherein the latch profile is located on a sleeve covering the ignition circuit.

9. The tubular string according to claim 8, wherein the latch profile is positioned between the propellant chamber and the ignition circuit.

10. A propellant tool for positioning in a wellbore, the tool comprising:
    a. a tubular body, the tubular body having a connector on each end for connection with other tubular members within a tubular string;
    b. a coded marker positioned on the tubular body;
    c. a propellant chamber positioned on an outside surface of the tubular body, wherein the propellant chamber includes a polymer sleeve extending over at least a portion of the tubular body and a propellant positioned in a space between the sleeve and outside surface of the tubular body; and
    d. a propellant ignition mechanism positioned on the tubular body.

11. The propellant tool according to claim 10, wherein the tubular body is formed of a non-magnetic material.

12. The propellant tool according to claim 10, wherein propellant chamber is positioned between the coded marker and the ignition mechanism.

13. The propellant tool according to claim 10, wherein the ignition mechanism is a circuit including a hand-shake sensor for confirming the presence of an activation plug.

14. The propellant tool according to claim 10, wherein the marker comprises multiple rings spaced along a length of the tubular body to create a distinct code readable as a reader passes through the tubular.

15. The propellant tool according to claim 10, wherein the propellant chamber comprises an annular structure formed around the tubular body.

16. The propellant tool according to claim 15, wherein the annular structure is formed of at least one of a carbon fiber material or a polymer material.

17. The propellant tool according to claim 10, wherein the propellant chamber comprises an annular structure formed of a polymer shell wall and the polymer shell wall includes at least one internal pocket containing an agent for dissolving the polymer.

18. The propellant tool according to claim 17, wherein the pocket has a lining resistant to the dissolving agent, wherein detonation of the tool ruptures the pocket and brings the dissolving agent into contact with the polymer.

19. The propellant tool according to claim 10, wherein the ignition mechanism is a circuit at least partially within an ignition housing positioned on an outer surface of the tubular body.

20. The propellant tool according to claim 10, further comprising an activation plug traveling into the tubular body and wherein an inner surface of the tubular body includes at least one latch profile configured to engage the activation plug.

21. The propellant tool according to claim 20, wherein the latch profile is positioned between the propellant chamber and the ignition mechanism.

22. The propellant tool according to claim 20, wherein the activation plug includes a reader capable of detecting the coded marker and deploying a set of keys to engage the latch profile in response to detecting the coded marker.

23. The propellant tool according to claim 22, wherein latch profile is formed on a sliding sleeve positioned within the tubular body.

24. The propellant tool according to claim 23, wherein the sleeve includes a first position covering the ignition mechanism and a second position uncovering the ignition mechanism.

25. The propellant tool according to claim 20, wherein the tubular body and the activation plug have circuitry adapted to transfer electrical power from the activation plug to operate a device on the tubular body.

26. The propellant tool according to claim 25, wherein the circuitry adapted to transfer electrical power includes induction coils in the tubular body and in the activation plug.

27. The propellant tool according to claim 25, wherein the transfer of electrical power is used to activate the firing mechanism.

28. The propellant tool according to claim 20, wherein the activation plug contains an explosive capable of destructing the plug.

29. The propellant tool according to claim 20, wherein the activation plug is formed of a drillable material.

30. The propellant tool according to claim 20, where the activation plug is formed of a dissolvable material and contains an encapsulated pocket with a dissolving agent, wherein the pocket is configured to rupture upon being subject to a pressure wave and allowing contact of the dissolving agent with the dissolvable material.

31. The propellant tool according to claim 10, wherein at least one burst disc is positioned in a wall of the tubular body.

32. The propellant tool according to claim 31, wherein a movable isolation sleeve covers the at least one burst disc.

33. The propellant tool according to claim 32, wherein the isolation sleeve includes a latch profile configured to be engaged by an activation plug traveling through the tubular body.

34. A propellant tool for positioning in a wellbore, the tool comprising:
   a. a tubular body, the tubular body having a connector on each end for connection with other tubular members within a tubular string;
   b. a propellant chamber including a sleeve positioned over an outside surface of the tubular body, the propellant chamber containing at least one propellant type positioned in a space between the sleeve and outside surface of the tubular body;
   c. a propellant ignition mechanism positioned on the tubular body and configured to ignite the propellant; and
   d. an event sensor coupled with a controller and a power source, the event sensor configured to activate the ignition mechanism upon the occurrence of a specified event.

35. The propellant tool according to claim 34, wherein the event sensor is at least one of (i) a pressure transducer configured to detect a coded sequence of pressure pulses and activate the ignition mechanism upon detection of the coded sequence; (ii) a seismic sensor configured to detect a seismic signal and activate the ignition mechanism upon detection of the seismic sensor; or (iii) a timer configured to active the ignition mechanism at some time subsequent to positioning of the propellant tool in the wellbore.

\* \* \* \* \*